US005176821A

United States Patent [19]
Forte

[11] Patent Number: 5,176,821
[45] Date of Patent: Jan. 5, 1993

[54] PROCESS FOR THE SEPARATION OF AROMATIC HYDROCARBONS WITH ENERGY REDISTRIBUTION

[75] Inventor: Paulino Forte, Yonkers, N.Y.

[73] Assignee: UOP, Des Plaines, Ill.

[21] Appl. No.: 657,916

[22] Filed: Feb. 20, 1991

[51] Int. Cl.⁵ ............................................. B01D 3/40
[52] U.S. Cl. .................................. 208/313; 208/321; 208/325; 208/333; 208/334
[58] Field of Search ............... 208/313, 318, 321, 325, 208/333, 334

[56] References Cited

U.S. PATENT DOCUMENTS

| | | | |
|---|---|---|---|
| 3,492,222 | 1/1970 | Van Tassell | 208/321 |
| 4,498,980 | 2/1985 | Forte | 208/321 |
| 4,664,786 | 5/1987 | Forte et al. | 208/356 |
| 4,690,733 | 9/1987 | Forte et al. | 203/21 |
| 4,693,810 | 9/1987 | Forte et al. | 208/321 |

OTHER PUBLICATIONS

Unit Processes and Principles of Chemical Engineering. Olsen, John C.
Handbook of Petroleum Refining Processes, published by McGraw-Hill Book Company, (1986), edited by Robert A. Meyers, pp. 8-53 to 8-60.

*Primary Examiner*—Theodore Morris
*Assistant Examiner*—William C. Diemler
*Attorney, Agent, or Firm*—Thomas K. McBride; John G. Tolomei; Richard P. Silverman

[57] ABSTRACT

In a combined solvent extraction/steam distillation process for the separation of aromatic hydrocarbons from a mixture of aromatic and non-aromatic hydrocarbons, there are three major thermal and material cycles: the solvent cycle, the hydrocarbon cycle, and the water cycle. The process is improved by redistributing the energy use between the three cycles to minimize the internal recycle within the process and to reduce the overall energy requirements. One means of the redistribution includes cooling of a lean solvent stream with liquid in a recovery or stripping column. Cooling of the lean solvent reduces flashing within an extract column and the resulting reflux of hydrocarbons to the extract column.

34 Claims, 3 Drawing Sheets

PROCESS FOR THE SEPARATION OF AROMATIC HYDROCARBONS WITH ENERGY REDISTRIBUTION

FIELD OF THE INVENTION

This invention relates to a continuous solvent extraction-steam-distillation processes for the recovery of aromatic hydrocarbons from a feedstream containing such aromatic hydrocarbons and non-aromatic hydrocarbons. The invention relates to the recovery of mixtures of benzene, toluene, xylenes (BTX) and other aromatics up to $C_{12}$ at purity levels required for petrochemical uses. More particularly, the subject invention relates to the redistribution of heat used within the process to achieve greater energy savings over conventional process arrangements.

BACKGROUND OF THE INVENTION

Conventional processes for the recovery of high purity aromatic hydrocarbons such as benzene, toluene and xylenes (BTX) from various hydrocarbon feedstocks including catalytic reformate, hydrogenated pyrolysis gasoline, etc., utilize an aromatic selective solvent. Typically, in the practice of such processes, a hydrocarbon feed mixture is contacted in an extraction zone with an aqueous solvent composition which selectively dissolves the aromatic components from the hydrocarbon feedstock, thereby forming a raffinate phase comprising one or more non-aromatic hydrocarbons, and an extract phase comprising solvent having aromatic components dissolved therein.

An important consideration in the design and operation of an aromatic extraction process beyond the recovery and the purity of the products is the operating cost. Excluding labor and capital charges, the major component of the operating cost is the energy requirements of the process. Because the products produced from this process are generally not finished products, but are often intermediate components for the blending of finished fuels and for the production of petrochemicals, any reduction in processing costs can translate into a significant economic advantage. An example of the energy costs for a conventional process for this application appeared in a discussion of the UOP Sulfolane Process which may be found on pages 8-53 to 8-60 in a book edited by Robert A. Meyers, entitled *Handbook of Petroleum Refining Processes*, published by McGraw-Hill Book Company, in 1986. In Table 8.4-1 on page 8-60 of this reference, the processing costs are presented for a 10,000 (B/D) barrel per day Sulfolane Unit producing 6,000 B/D of BTX extract. The energy costs, comprising steam, electric power and cooling water amounted to 83% of the total processing cost on a daily basis, expressed in monitory units. Solvent make-up charges were 2%. Labor and maintenance costs made up the remaining 15%.

In commercial practice the amount of energy used by aromatics extraction processes range from 600-900 BTU's (British Thermal Units) per pound of aromatic material extracted. When one considers that the recovery of aromatic hydrocarbons involves the use of three major material cycles, typically hydrocarbon, water, and solvent, there are numerous possibilities within the process for the management of energy as these materials are vaporized and condensed to affect the separation.

A number of examples have been developed to achieve energy savings using continuous solvent extraction-steam-distillation for the recovery of aromatic hydrocarbons. Representative examples are believed to be presented in U.S. Pat. Nos. 4,690,733; 4,693,810 and 4,664,786. The U.S. Pat. No. 4,690,733, issued to Forte et al., shows an aromatics extraction process segment wherein high pressure steam is fed to a steam ejector and the resulting steam is employed in a first heat exchanger to provide heat to reboil a distillation column for the recovery of lean solvent and in a second heat exchanger to transfer heat from the recovered lean solvent to the condensate from the first heat exchanger before returning the condensate to the steam ejector to complete the steam generation cycle. The process is claimed to lower energy costs by reducing reflux to feed ratios in the extractor and lowering solvent recirculation rates. Capital costs are increased by the addition of the steam ejector and an additional heat exchange is required over conventional practice.

In the U.S. Pat. No. 4,693,810 to Forte et al., the stripping water is divided into two streams. One stream is passed to a motive steam generator to vaporize the water and then passed to a steam ejector. The second stream is passed to a heat exchanger wherein heat is transferred from a lean solvent stream to vaporize all of the stripping water rather than just a portion and return the water vapor to the stripping column by means of the steam ejector. Capital costs are increased by the cost of the steam generator, steam ejector, and additional heat exchanger.

In the U.S. Pat. No. 4,664,786 to Forte et al. stripping water is recycled to a steam distillation zone while heat recovered from an overhead stream is used to vaporize the stripping water using a motive steam generator to pump stripping water vapors into the stripping column.

An essential objective in reducing the overall energy requirements of the process is to minimize the amount of heat withdrawn from the process to the environment as in cooling, or condensing of process streams. The condenser duty translates into the amount of energy that cannot be recovered, that is lost or taken out of the process. By lowering the temperature of the lean solvent, the selectivity of the solvent is improved and the amount of non-aromatics extracted with the aromatics is reduced, reducing the overall energy consumption.

SUMMARY OF THE INVENTION

An object of this invention is to improve the redistribution of the of heat in a process for the recovery of aromatic hydrocarbons.

Another object of this invention is to reduce the amount of recycle to an extraction zone.

A yet further object of this invention is to reduce the flashing solvent in a recovery zone.

This invention reduces the energy consumed by a series of two distillation zones in an aromatic solvent extraction process by transferring heat from a lean solvent stream to an intermediate portion of one of the distillation zones via a closed heat exchange loop or an interheater. In addition, heat exchange of lean solvent in the manner of this invention decreases the temperatures of the feeds to the stripping zone and the recovery zone which surprisingly reduces the amount of recycle comprising light non-aromatic hydrocarbons returned to the extractor. Operation of the stripper column and recovery column were enhanced at the lower feed temperatures to reduce the amount of internal reflux in the columns. Stripping steam for the recovery column was generated by transferring heat from the rich solvent stream, permitting the substantial temperature and heat content of the lean solvent to provide heat for liquids within either the recovery column or as an alternate, the stripper column, reducing the condenser duties required for the overall process. The condenser duties in the stripper column and the recovery column are established by an overall energy balance within each column. By using the lean solvent to transfer heat already in the process to liquid within these columns, the amount of energy required to be removed from the overall process is reduced. Reducing the condenser duties and reducing the amount of recycle resulted in significant energy savings.

In one embodiment this invention is a continuous extraction-steam distillation process for the separation of aromatic hydrocarbons from a feedstock comprising non-aromatic hydrocarbons and aromatic hydrocarbons. In this embodiment a feedstock containing aromatic hydrocarbons and non-aromatic hydrocarbons is contacted with a lean solvent stream and a recycle stream in an extractor zone at super atmospheric pressure. The extraction operation separates the feedstock into a raffinate stream comprising light non-aromatic hydrocarbons and a first rich solvent stream comprising solvent, aromatic hydrocarbons and at least a portion of the light non-aromatic hydrocarbons. The first rich solvent stream is heated in a first heat exchanger. From the heat exchanger, the rich solvent is passed to a stripper zone. The stripper zone is operated at a pressure near atmospheric pressure to produce a first vapor stream comprising light non-aromatic hydrocarbons, aromatic hydrocarbons, and water, and a second rich solvent stream. The first vapor stream is condensed and divided into a mixed hydrocarbon phase and a first water rich phase. At least a portion of the mixed hydrocarbon phase is recycled to the extractor zone as a recycle stream to improve the separation in the bottom of the extractor zone. At least a portion of the second rich solvent stream is passed to a second heat exchanger and cooled therein. In the second heat exchanger a portion of the heat from the second rich solvent stream is used to heat a wash water stream and produce stripping steam for a recovery zone. The cooled second rich solvent stream is passed to a feedpoint in the recovery zone. The recovery zone is operated to produce a second vapor stream comprising aromatic hydrocarbons and water, and a bottoms product comprising lean solvent. The second vapor stream is condensed and at least a portion of the aromatic hydrocarbon rich phase is recovered as an extract product stream. A lean solvent stream is recovered from the recovery zone and passes to a heat exchange device wherein heat is transferred to liquid within the recovery zone at or below the feedpoint to at least partially vaporize the liquid in the recovery zone. Heat transfer in the recovery zone may be accomplished by a device within the zone, or an external heat exchanger where liquid is withdrawn from the zone and passed to a heat exchanger. The partially vaporized zone liquid is usually returned to the zone at a point above where it was withdrawn. Following the heat exchange with liquid within the recovery zone, the lean solvent is passed to the first heat exchanger wherein heat is exchanged with the first rich solvent stream. From the first heat exchanger, the lean solvent is introduced to the top of the extractor zone.

In another arrangement of the invention, the lean solvent stream is not cooled with recovery zone liquid, but is instead used to provide heat transfer to liquid within the stripper zone at a location between the feedpoint of the rich solvent. Thus, the heat exchange device operates on fluid in the stripping zone. The heat exchange device may be a third heat exchanger used to exchange heat between the lean solvent stream and the liquid within the stripper zone. The stripper zone liquid withdrawn for heat exchange is usually returned at a point below where it was withdrawn. As in the previous embodiment, the lean solvent is then passed to the first heat exchanger wherein it exchanges heat with the rich solvent from the extractor zone. The lean solvent is again passed from the first heat exchanger to the extractor zone.

DETAILED DESCRIPTION OF THE INVENTION

Figure 1:
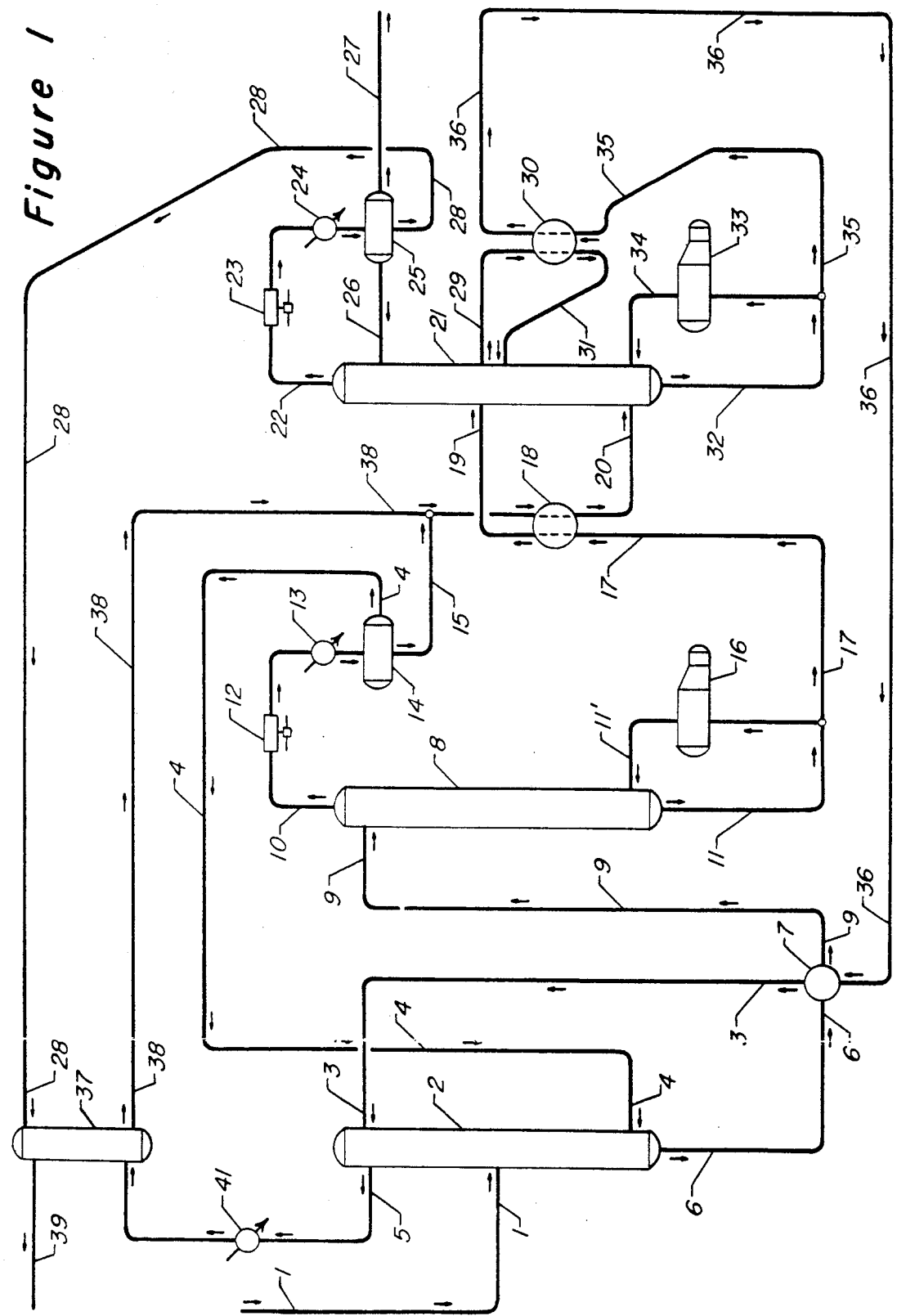
FIG. 1 is a schematic flow diagram of the process of the invention showing a specific arrangement for heat exchange about a recovery column.

Hydrocarbon feedstocks suitable for utilization in the method of the present invention include many different aromatic-non-aromatic mixtures having a substantially high enough concentration of aromatic hydrocarbons to economically justify the recovery of the aromatic hydrocarbons as a separate product stream. The present invention is particularly applicable to hydrocarbon feed mixtures containing at least 15% by weight aromatic hydrocarbons. Typical aromatic feedstock charged to an extraction step will contain from about 25% to about 80% by weight aromatic hydrocarbons with aromatic hydrocarbon concentrations as high as 98% being suitable in some instances. A suitable carbon range for the hydrocarbon feedstock is from about 5 carbon atoms per molecule to about 20 carbon atoms per molecule, and preferably from 5 to 12 carbon atoms per molecule.

One suitable source of hydrocarbon feedstock is a depentanized fraction from the effluent from a conventional catalytic reforming process unit for the reforming of a naphtha feedstock. Another suitable source of feedstock is the liquid by-product from a pyrolysis gasoline unit which has been hydrotreated to saturate olefins and diolefins, thereby producing an aromatic hydrocarbon concentrate suitable for the solvent extraction technique described herein.

A preferred feedstock for use in the present invention is one recovered from a catalytic reforming unit, comprises single ring aromatic hydrocarbons of the $C_6$-$C_{10}$ range which are also mixed with corresponding boiling range paraffins and naphthenes which are present in the product from a catalytic reforming unit.

Solvent compositions which may be utilized in the practice of the present invention are those selected from the classes which have high selectivity for aromatic hydrocarbons. These aromatic selective solvents generally contain one or more organic compounds containing in their molecule at least one polar group, such as a hydroxyl, amino, cyano, carboxyl or nitro radical. In order to be effective, the organic compounds of the solvent composition having the polar radical must have a boiling point substantially greater than the boiling point of water since water is typically included in the solvent composition for enhancing its selectivity. In general, the solvent must also have a boiling point greater than the end boiling point of the aromatic component to be extracted from the hydrocarbon feed mixture.

Organic compounds suitable for use as part of the solvent composition are preferably selected from the group of those organic-containing compounds which include the aliphatic and cyclic alcohols, cyclic monomeric sulfones, the glycols and glycol ethers, as well as the glycol esters and glycol ether esters. The mono- and poly-alkylene glycols in which the alkylene group contains from 2 to 3 carbon atoms, such as ethylene glycol, diethylene glycol, triethylene glycol, and tetraethylene glycol, propylene glycol, dipropylene glycol, and tripropylene glycol, as well as the methyl, ethyl, propyl and butyl ethers of the glycol hydroxyl groups and the acetic acid esters and mixtures of the above, constitute a satisfactory class of organic solvents useful in admixture with water as the solvent composition for use in the present invention.

Some of these solvents, when combined with other cosolvents, can provide mixed extraction solvents having desirable properties. When such mixed solvents are utilized, the preferred solvents are the low molecular weight polyalkylene glycols of the formula:

HO—[CHR$_1$—(CR$_2$R$_3$)$_n$—O]$_m$—H wherein n is an integer from 1 to 5 and is preferably the integer of 1 or 2; m is an integer having a value of 1 or greater, preferably between about 2 to about 20 and most preferably between about 3 and about 8; and wherein R$_1$, R$_2$ and R$_3$ may be hydrogen, alkyl, aryl, aralkyl or alkylaryl and are preferably hydrogen and alkyl having between 1 and about 10 carbon atoms and most preferably are hydrogen. Examples of the polyalkylene glycol solvents employable herein are diethylene glycol, triethylene glycol, 1,3-butylene glycol, 1,2-butylene glycol, 1,5-pentaethylene glycol, and mixtures thereof and the like. Preferred solvents are diethylene glycol, triethylene glycol, tetraethylene glycol being most preferred. When a "cosolvent" component is employed herein such is preferably a glycol ether of the formula:

R$_4$O—[CHR$_5$—(CHR$_6$—)—$_x$O]$_y$—R$_7$ wherein R$_4$, R$_5$, R$_6$ and R$_7$ may be hydrogen alkyl, aryl, aralkyl, alkylaryl and mixtures thereof with the provisio that R$_4$ or R$_7$ are not both hydrogen. The value of x is an integer from 1 to 5, preferably 1 or 2 and y may be an integer from 1 to 10 and is preferably from 2 to 7, and most preferably from 2 to 5. R$_4$, R$_5$, R$_6$ and R$_7$ are preferably selected from the group consisting of hydrogen and alkyl having 1 to about 10 carbons with the provisio that R$_4$ and R$_7$ may not both be hydrogen and most preferably R$_4$ is alkyl having from 1 to 5 carbons and R$_5$, R$_6$ and R$_7$ are hydrogen. The mixture(s) of solvent and cosolvent is selected such that at least one solvent and one cosolvent are provided to form the mixed extraction solvent. The cosolvent generally comprises between about 0.1 and about 99 percent of the mixed extraction solvent, preferably between about 0.5 and about 80 percent and more preferably between about 5 and about 60 percent by weight based on the total weight of the mixed extraction solvent. The above-described mixed extraction solvents are fully disclosed in U.S. Pat. No. 4,498,980, hereby incorporated by reference.

Another typical aromatics-selective solvent utilized in commercial aromatic extraction processes which can be recovered in accordance with the practice of this invention, is commonly referred to as sulfolane (tetrahydrothiphene,1-1 dioxide). Also employed are those sulfolane derivatives corresponding to the structural formula:

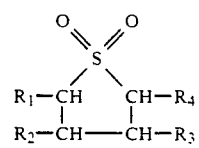

wherein R$_1$, R$_2$, R$_3$ and R$_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms. Other solvents which may be included within this process are the sulfolenes, such as 2-sulfolene or 3-sulfolene which have the following structures:

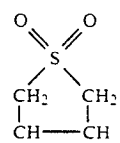

Other typical solvents which have a high selectivity for separating aromatics from non-aromatic hydrocarbons and which may be processed within the scope of the present invention are 2-methysulfolane, 2,4-dimethylsulfolane, methyl-2-sulfonyl ether, N-aryl-3-sulfonylamine, 2-sulfonyl acetate, dimethylsulfoxide, N-methyl pyrrolidone, etc.

A particularly preferred solvent of the above-described sulfolane type has the following structural formula:

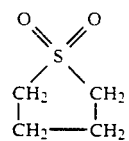

The aromatic selectivity of the solvent can usually be enhanced by the addition of water to the solvent. The solvents utilized in the practice of this invention could contain small quantities of water in order to increase the selectivity of the overall solvent phase for aromatic hydrocarbons without reducing substantially the solubility of the solvent of the solvent phase for aromatic hydrocarbons. Accordingly, the solvent composition of the present invention preferably contains from about 0.1% to about 20% by weight water and, preferably, about 0.5 to about 10% by weight depending upon the particular solvent utilized and the process conditions at which the extraction zone and the extractor-stripper are operated.

Aromatic hydrocarbons contained in the foregoing feedstocks are recovered by introducing the hydrocarbon feedstock into a solvent extraction zone maintained under solvent extraction conditions including the presence of an aromatic selective solvent of the type discussed. Solvent extraction conditions and techniques are generally well known to those trained in the art and vary, depending on the particular aromatic selective solvent utilized.

The solvent extraction zone provides an extract phase comprising solvent having aromatic hydrocarbons and a minor amount of non-aromatic hydrocarbons dissolved therein and a raffinate phase comprising non-aromatic hydrocarbons. Typically, the raffinate is water washed to remove any solvent which may be in solution and entrained therein. In the present invention, this water is preferably provided by the aqueous overhead condensate from a rectification zone as hereinafter described. Preferably, the extraction conditions utilized are correlated to maintain the solvent and hydrocarbons passed to the extraction zone in the liquid phase so as to embody a liquid phase solvent extraction. The conditions, apparatus, and mode of operation associated with the solvent extraction zone are well known to those trained in the art. For example, see U.S. Pat. Nos. 3,702,295; 3,714,003; 4,419,226; and 4,781,820, hereby incorporated by reference.

Also embodied within the solvent extraction zone is the concept of displacing heavier non-aromatic hydrocarbons from the extract phase at the lower end of the solvent extraction zone by utilizing the known technique of a recycling from the overhead of the stripping column hydrocarbon containing recycle at that point. By displacing the heavy non-aromatics with light non-aromatics, the resulting non-aromatics are more readily separable from the aromatics in the subsequent stripping zone to be discussed later. It is preferred that this recycle stream comprise relatively light non-aromatic hydrocarbons but significant quantities of aromatic hydrocarbons, i.e., 30% to 60% by weight, may be present in the recycle stream. The exact amount of recycle introduced into the lower section of the solvent extraction zone varies depending on the degree of non-aromatic hydrocarbon rejection desired in the extraction zone. Preferably, the recycle is at least 10% by volume of the extract phase so as to insure effective displacement of the heavy non-aromatic hydrocarbons from the extract phase into the raffinate. According to the process of the present invention at least a portion, if not all, of the light non-aromatic recycle required is provided by a non-aromatic fraction removed as overhead from an upper section of a hereinafter described stripping zone, usually comprising a single column. This fraction is withdrawn as a vapor and contains water (steam) which is preferably condensed and removed before the non-aromatics are passed as recycle to the solvent extraction zone, usually comprising a single extractor column which is also referred to as an extractor.

The solvent extraction zone is operated under conventional conditions including a temperature and a sufficiently elevated pressure to maintain the solvent, the recycle, and the hydrocarbon charge stream in the liquid phase. When utilizing a solvent such as sulfolane, suitable temperatures are about 80° F. to about 400° F., preferably about 175° F. to about 300° F., and suitable pressures are about atomospheric to about 400 psig, preferably about 50 to 150 psig. Solvent quantities should be sufficient to dissolve substantially all of the aromatic hydrocarbons present in the hydrocarbon feed to the extraction zone. Preferred are solvent to feed ratios, by volume, of about 2:1 to about 10:1 when utilizing a $C_6$-$C_{10}$ range naphtha cut as feed.

The extract phase from the solvent extraction zone comprising solvent, aromatic hydrocarbons and contaminating non-aromatic hydrocarbons is introduced into an upper section of a stripper zone to remove therein, the non-aromatic hydrocarbons. This separation is accomplished by fractionation to remove essentially all of the contaminating amounts of non-aromatic hydrocarbons from the extract phase as a vapor fraction which is withdrawn from the upper section of the stripping zone. This vapor fraction comprises water (steam), non-aromatic hydrocarbons, and an amount of aromatic hydrocarbons. This vapor fraction is preferably cooled and condensed to form an aqueous phase and a hydrocarbon phase. This hydrocarbon phase is then recovered and passed to the lower section of the solvent extraction zone to serve as the described light non-aromatic recycle and to recover the aromatic hydrocarbons contained in the original vapor fraction withdrawn from the upper portion of the stripping zone. The aromatic hydrocarbons are then recovered from the bottom of the stripping zone as a liquid in a rich solvent stream comprising aromatic hydrocarbons and solvent.

The liquid stream comprising aromatics and solvent from the bottom of the stripper zone is introduced at a feedpoint to a recovery zone for the separation of the aromatic extract product from the solvent. A vapor fraction essentially free of solvent, comprising aromatic hydrocarbons and water vapor is withdrawn from the top of the recovery column. The vapor fraction is condensed and two liquid phases are recovered, i.e., an aromatic phase essentially free of non-aromatics, and a second water phase.

As is well known to those trained in the art, exact processing conditions are a function of a myriad of variables, particularly feed compositions, aromatic purity desired and aromatic recovery sought. However, the conditions to be utilized in a stripper zone of the type described are broadly within a temperature range of about 180° F. to about 500° F., typically 320°F. to 380° F. at the bottom of stripper zone and a pressure near atmospheric pressure. A near atmospheric pressure range for this invention shall mean about 500 mmHg absolute to about 50 psig and more preferably from about 1 psig to about 20 psig. Stripping medium, e.g., steam comprising raffinate wash water and aqueous overhead condensate from the stripper zone is introduced to the recovery column at a temperature between 100° F. and 250° F. The rich solvent feed is introduced to the recovery column typically at a pressure at or above atmospheric pressure and a temperature of 200°-320° F. The recovery column overhead accumulator is controlled to a temperature of approximately 100° F. The rectification zone of the recovery column is typically maintained at a pressure of from 200 mmHg to 10 psig, typically about 450 mmHg, and a temperature of from 180°-500° F., typically, about 350° F. at the drawoff point for lean solvent. Based on the teaching herein, it is within the scope of one trained in the art to readily develop more specific processing conditions for a given feedstock.

At least a portion of the water phase from the recovery column is usually returned to an upper section of a raffinate column wherein the water is used to wash the raffinate from the extractor. At least a portion, and preferably all, of the spent wash water from the raffinate column is returned to a heat exchanger wherein the water is vaporized by transferring heat from the stripper column bottom stream prior to introducing the steam to a point in the lower section of the recovery column as a stripping medium.

In one aspect of the present invention at least a portion, and preferably all, of the lean solvent from the recovery zone is then passed to a heat exchanger whereby heat is transferred to the fluid within the rectification section of the recovery zone at a point below the feedpoint of the rich solvent from the stripper zone and above a point where reboiled lean solvent is returned to the bottom of the recovery column. It is to be noted that the stripping zone bottoms can be heat-exchanged with other streams, e.g., the spent wash water stream to vaporize the stripping medium prior to introducing it into the recovery zone. This reduces or eliminates the flashing of solvent in the recovery zone which further permits a significant reduction in the amount of recovery column reflux required to keep the extract product essentially free of solvent, thus reducing the energy required for the separation. Compared to the prior art, a lowering of the temperature of the rich solvent feed from the extractor to the stripper zone also occurs. The resultant lower rich solvent temperature reduces its flashing as it enters the stripping zone; thus, resulting in a reduced amount of recycle to the extractor. The lowering of the reflux in the recovery zone, and the reduction of recycle to the extractor results in a reduction of the total energy required by the process.

In another aspect of the invention, following the vaporization of the wash water with the rich solvent stream from the stripper zone, the substantial temperature and heat content of the lean solvent stream from the recovery zone may be used to partially reboil the stripper zone. It is contemplated that reboiling with the lean solvent supplements the operation of a reboiler in the stripping zone. Transferring heat to the liquid within the stripper zone is best accomplished by heat exchange with the lean solvent at a point above the stripper reboiler and below the point where the rich solvent enters the stripping zone. The transfer of heat from the lean solvent to partially reboil the stripper zone has the effect of lowering the temperature of the rich solvent feed to the stripper zone. Also the stripper bottoms is used to vaporize the stripping water, lowering its temperature, thus reducing the flashing of the solvent in the recovery zone. This reduction in recycle to the extractor and the reduced flashing of the feeds to the stripper zone and recovery zone results in significant energy savings.

When the three zone system is operated in three separate columns, the number of theoretical stages or trays required to achieve the degree of fractionation is as follows:

|  | No. of Theoretical Stages |
| --- | --- |
| Extractor Column | 6–18 |
| Stripper Column | 6–18 |
| Recovery Column | 10–30 |

The number of stages selected for an individual process will depend somewhat upon the composition of the hydrocarbon feedstock and the content of aromatic hydrocarbons. The actual number of trays in each column will depend further upon the efficiency of the tray design employed for the separation. Typically, trays efficiencies for these separations range from 40–60%.

Figure 2:
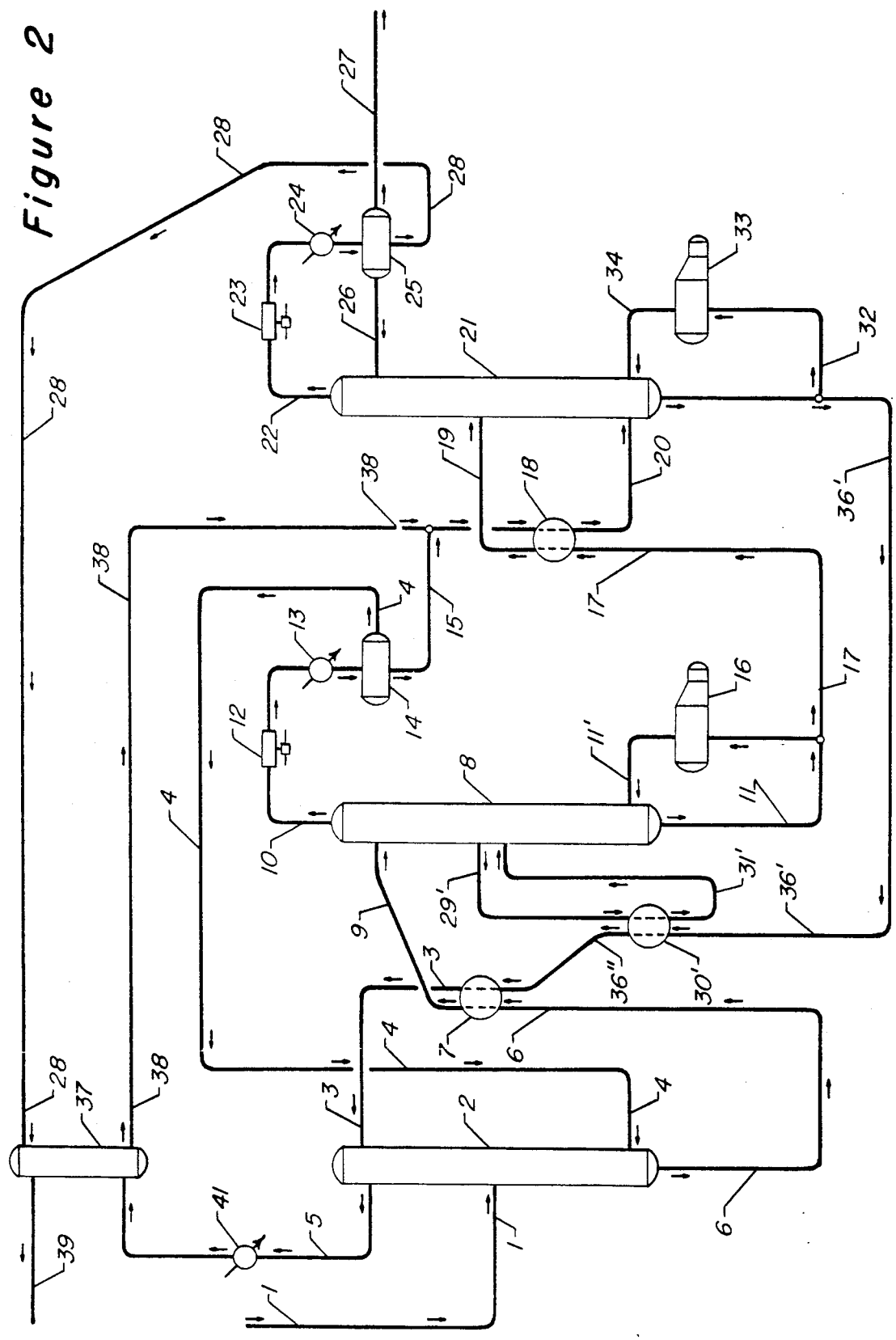
FIG. 2 is a schematic flow diagram showing a more limited embodiment of this invention.

The further description of the method of this invention is presented with reference to the attached schematics, FIG. 1 and FIG. 2. The figures represent preferred arrangements of the invention and are not intended to be a limitation on the generally broad scope of the invention as set forth in the claims. Of necessity, some miscellaneous appurtenances including valves, pumps, separators, heat exchangers, reboilers, etc., have been eliminated. Only those vessels and lines necessary for a complete and clear understanding of the process of the present invention are illustrated, with any obvious modifications made by those possessing expertise in the art of aromatic solvent extraction.

Referring to FIG. 1, a $C_6$–$C_{12}$ cut of depentanized reformate containing aromatic hydrocarbons and non-aromatic hydrocarbons is passed via line 1 to extractor 2 maintained at extraction conditions, along with lean solvent via line 3 and reflux via line 4, the sources of which are hereinafter described. A raffinate stream comprising non-aromatic hydrocarbons and solvent are removed from extractor 2 via line 5, cooled in heat exchanger 41 to separate a portion of the dissolved solvent out of solution (not shown), said recovered solvent can be recycled to extractor 2 and introduced (not shown) at or near the feedpoint of line 1. Alternatively, this stream can be added to the lean solvent stream, line 3. The hydrocarbon raffinate phase can then be washed with water from the overhead aqueous phase condensate of the recovery column 21. This overhead aqueous phase is carried by line 28 and is substantially free of solvent. A rich solvent stream containing aromatic hydrocarbons, non-aromatic hydrocarbons, solvent and water is removed from extractor 2 via line 6 and passed to a heat exchanger 7 where heat is transferred from lean solvent stream 36 to rich solvent stream 9. A rich solvent stream 9 is then passed to an upper section of stripper column 8, which is essentially a distillation zone containing at least one vaporizing section which functions to flash off and vaporize water, aromatics, and a portion of the non-aromatic hydrocarbon contaminants contained in the extract phase in line 9.

The rich solvent phase from line 9 is introduced into the upper section of column 8 at super-atmospheric pressure, e.g., 25 psig and a temperature of about 200° F. to about 250° F. Under these conditions, a portion of the aromatics and a portion of the non-aromatic hydrocarbons are flashed off and removed via line 10. The overhead vapor stream 10 is cooled and condensed via air cooler 12 and trim cooler 13 to produce a light hydrocarbon rich phase comprising light non-aromatic hydrocarbons which is returned to the extractor column 2. Other arrangements may employ either an air cooler or a water cooler to condense the vapor. The bottom of the stripper column 8 is reboiled with reboiler 16 providing heat to reboil stream 11 and return it to the stripper via line 11'. The residue of the extract stream, or rich solvent now comprising solvent having the desired aromatic hydrocarbons dissolved therein is taken from line 11 via line 17 to heat exchanger 18. In exchanger 18, the large heat content of rich solvent stream 17 is used to vaporize stripping medium comprising raffinate wash water from line 38 and aqueous stripper overhead condensate from line 15. The stripping medium is then introduced to the recovery column 21 as stripping steam by line 20 near the bottom of the recovery column. A cooler rich solvent stream 19 is introduced as feed to the recovery column 21 at a feedpoint above where the stripping medium of line 20 was introduced. A liquid stream 32 comprising lean solvent is withdrawn from the bottom of the recovery column 21 and a portion is reboiled in reboiler 33 and returned to the bottom of the recovery column 21 via line 34. All or a portion of a lean solvent 35 is then passed to a heat exchanger 30 to exchange heat or reboil a liquid stream 29. Stream 29 and exchanger 30 represent the heating of liquid inside the recovery column located at or below the point where the rich solvent stream 19 was introduced as feed and above the point where the reboiled stream 34 was reintroduced to the recovery column. The preferred method for the heat transfer between the lean solvent 35 and the liquid stream 29 in the recovery column is with a column interheater located inside the recovery column (schematically shown outside the column as exchanger 30) below the feedpoint of stream 19 and above the return point of line 34. Also, an external countercurrent heat exchanger may be employed. Following the heat exchange in heat exchanger 30, the heated, and partially vaporized stream 31 is returned to the column at or below the point from where it was withdrawn, but preferably at or below the feedpoint. The overhead vapor stream 22 is condensed via condenser 23 and a trim cooler 24. Cooling and condensation of the vapor results in the formation of an aromatic extract phase and an aqueous phase in an overhead accumulator 25. The extract product is withdrawn as a stream 27. A portion of the overhead hydrocarbon or aqueous condensate is returned to the recovery column 21 via line 26 as internal reflux. The remainder, carried by line 28, is preferably used as raffinate wash water. The water phase of line 28 is preferentially used as the raffinate wash water to wash the raffinate of stream 5 in a raffinate column 37. Stream 5 enters column 41 after cooling in an exchanger 41. Solvent-free raffinate product stream 39 is withdrawn from the top of the raffinate column 37, and a raffinate wash water stream 38 is withdrawn from the bottom of the raffinate column 37 and used as stripping medium in recovery column 21.

The lean solvent from exchanger 30 is taken by a line 36 and passed to a heat exchanger 7 to exchange heat with the rich solvent stream 6. The cooled lean solvent stream is passed to the extractor 2 as before herein described.

Referring to FIG. 2, an alternate arrangement of the invention is described. The description hereinbefore presented with reference to FIG. 1 is applicable here unless otherwise set forth below. In the arrangement of FIG. 2, the lean solvent stream or recovery column bottoms, carried by a line 36', are not used to exchange heat with liquids in the recovery column 21, but are instead used to provide a portion of its heat to the stripper column 8 by exchanging heat with liquid, illustrated as carried by a line 29, within the column 8 at a point located above the return of the reboiled stream 11' by means of a heat exchanger 30' (schematically shown outside the column). The preferred method for transferring heat to the stripper column 8 is by means of an interheater. Exchanger 30' may represent such an interheater or an external countercurrent heat exchanger. A partially reboiled liquid stream 31' from exchanger 30' is returned to the stripper column at a point below the point from where it was withdrawn and preferably below the column entry point of stream 9. The cooler lean solvent stream from exchanger 30' is passed via a line 36" to heat exchanger 7 where it transfers heat to the rich solvent stream 6. The lean solvent in line 3 is passed from heat exchanger 7 to the extractor column. This alternative operation uses essentially similar operating ranges of pressure, temperature and recovery as the arrangement presented in FIG. 1.

EXAMPLE 1

Figure 3:
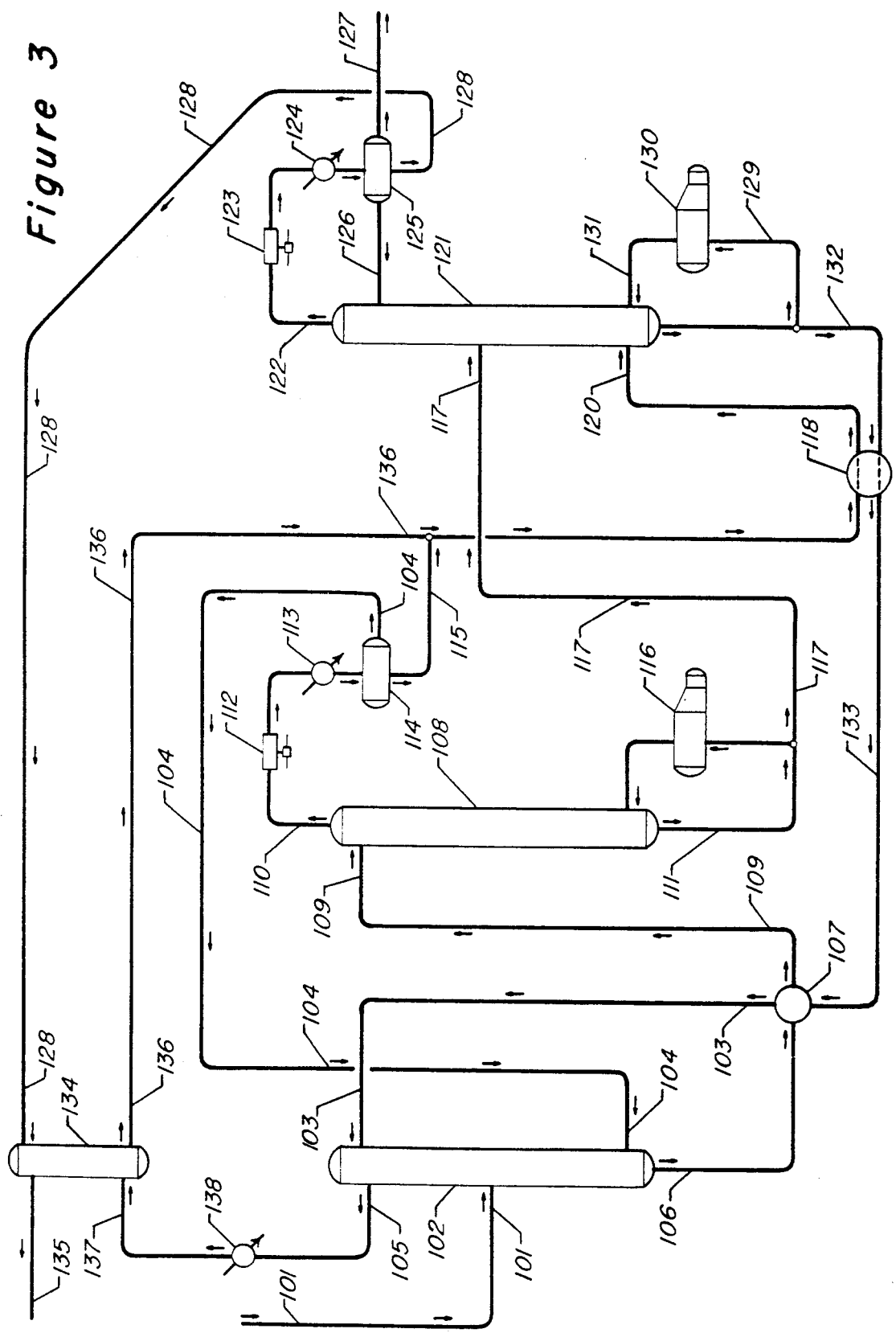
FIG. 3 is a schematic flow diagram showing the basic arrangement for a typical prior art aromatics extraction process.

The following data illustrates the type of results that can be obtained by practicing a prior art process using the basic scheme for the sulfolane aromatics extraction process depicted in FIG. 3.

The basic scheme for a sulfolane process for the extraction of a feedstream containing aromatic hydrocarbons from a mixed stream comprised of aromatic and non-aromatic hydrocarbons is shown in FIG. 3. Referring to FIG. 3, a feedstream 101 is introduced to an extractor column 102 along with a lean sulfolane solvent stream 103 and a process recycle stream 104 at appropriate extraction conditions. A raffinate stream 105 comprising non-aromatic hydrocarbons is removed overhead and a rich solvent stream 106 is removed from the bottom of the extractor 102. The rich solvent stream 106 is heat exchanged with a lean solvent stream 133 and the rich solvent stream 109 is passed as feed to a stripper column 108. The stripper column 108 produces an overhead stream 110 comprising light non-aromatic hydrocarbons and water. Following the condensation of the stripper overhead stream 110 via air cooler 112 and trim cooler 113, the stream is passed to an overhead accumulator 114 wherein a hydrocarbon phase and a water phase form. The hydrocarbon phase is passed by line 104 to the extractor column 102 as a recycle stream and the water phase is passed by line 115 to a point where it is combined with a spent raffinate wash water stream 136 and passed to a second heat exchanger 118 where in the combined aqueous streams 115 and 136 are vaporized to provide stripping medium or steam to the lower section of a recovery column 121. The heat of vaporization for the aqueous streams is provided by the heat transferred from a lean solvent stream 132. A rich solvent stream 117, depleted of substantially all of the light non-aromatic hydrocarbons is passed to column 121 at a feedpoint above the point of introduction of a stripping steam stream 120. The recovery column overhead 122 is condensed by air cooler 123 and trim cooler 124 and collected in accumulator 125 wherein a hydrocarbon phase and a water phase are separated. The hydrocarbon phase comprising an aromatic hydrocarbon extract stream 127 is withdrawn as product and a water phase stream 128 is withdrawn for use in the raffinate column 134 to wash the raffinate stream 105 from the extractor column 102. Following a reduction in temperature in heat exchanger 138, the raffinate stream is carried by a line 137 and introduced at the bottom of the raffinate column 134. The wash water 136 is withdrawn from the lower section of the recovery column and combined with the first aqueous phase 115 from the stripper column 108 to provide stripping medium to produce a stripping steam stream 120 in heat exchanger 118.

The lean solvent is withdrawn from the bottom of the recovery column and is passed via a line 132 to exchanger 118 wherein heat is transferred to the stripping medium as discussed herein. The lean solvent is then passed to heat exchanger 107 wherein heat is transferred to the rich solvent 106, further reducing the temperature of the lean solvent 103 before it is introduced to the top of the extractor column 102.

The data corresponding to these and other examples are obtained from computer simulations of the process for treating a feedstream composed of about 14.9 wt. % pentane; 14.6 wt. % benzene; 49.1 wt. % toluene; 12.6 wt. % hexane; 4.60 wt. % heptane; 1.33 wt. % octane; 1.11 wt. % cyclopentane; 0.51 wt. % methylcyclopentane; 0.34 wt. % methylcyclohexane. Total aromatics in the feed is 64.1 wt. %. The temperature of the feed prior to entry in the extractor is 80° F. and pressure of 140 psia.

The feed rate as based on a commercial size unit is 94,000 lb/hr and the extract rate is 60,839 lb/hr. The temperature of the rich solvent stream 109 to the stripper is 232° F. and the temperature of the rich solvent stream 117 to the recovery column is 350° F.

Table 1 sets forth the results of the heat and material balance for the basic case. The energy required to operate the process was 32 million BTU/hr, equivalent to 526 BTU/lb of aromatic hydrocarbons extracted in line 127.

EXAMPLE 2

In practicing the teachings of this invention as depicted in FIG. 1, the feed rate and product rates are maintained to be the same as in Example 1. The feedstock is introduced to the extractor at the same conditions. The data for this scheme is shown in Table 1, column 2. In the scheme as shown in FIG. 1, the temperature of the rich solvent stream 9 feed to the stripper column 8 is reduced by between 35° and 40° F. and the temperature of the rich solvent stream to the recovery column 21 is reduced by about 80° F. in comparison to Example 1. Furthermore, the reflux stream 4 is reduced by over 33%. These changes reduce the total heat required to 27.1 million BTU/hr and reduce the heat required per unit of extract product of line 27 to 446 BTU/lb which represents an improvement of over 15% in energy savings.

EXAMPLE 3

The following data illustrate the type of results that can be obtained by practicing the teachings of an alternate scheme of this invention as shown in FIG. 2.

As in Example 1, all flows of feedstock and product were maintained at the same rates and conditions. In this scheme the temperature of the rich solvent stream 9 is reduced from the basic scheme by between 10° and 20° F. and the temperature of the feed to the recovery column 21 is reduced by between 70° and 75° F. It was also required to increase the number of stages in the recovery column by 1 to maintain the separation. In Example 3 the the reflux is reduced by 20-25%. These changes reduce the total heat required to 27.8 million BTU/hr and reduce the heat required per unit of extract product of line 27 to 457 BTU/lb which represents an improvement of over 13% in energy saved.

TABLE I

| FEED = 64.1 wt % AROMATICS | | | |
|---|---|---|---|
| | EXAMPLE 1 PRIOR ART To FIG. 3 | EXAMPLE 2 INVENTION To FIG. 1 | EXAMPLE 3 INVENTION To FIG. 2 |
| A. EXTRACTOR | | | |
| 1. Feed Rate, lb/hr | 94,000 | 94,000 | 94,000 |
| 2. Solvent/Feed, wt/wt | 3.0 | 3.0 | 3.0 |
| 3. Reflux/Feed, wt/wt | 0.34 | 0.23 | 0.26 |
| 4. Lean Solvent Temperature, °F. | 190 | 190 | 190 |
| B. STRIPPER COLUMN | | | |
| 1. Top Pressure, psig | 18 | 7.5 | 9 |
| 2. Bottom Pressure, psig | 23 | 12.5 | 4 |
| 3. Bottom Temperature, °F. | 350 | 310 | 316 |
| 4. Reboiler Duty, MMBTU/hr | 24.1 | 20.9 | 10.3 |
| 5. Feed temperature, °F. | 232 | 196 | 217 |
| C. RECOVERY COLUMN | | | |
| 1. Top Pressure, mmHg | 300 | 300 | 300 |
| 2. Bottom Pressure, mmHg | 440 | 440 | 440 |
| 3. Reboiler Duty, MMBTU/hr | 7.9 | 6.2 | 17.5 |
| 4. Feed Temperature, °F. | 350 | 270 | 276 |
| 5. Reflux Ratio, mole/mole | 0.30 | 0.18 | 0.18 |
| C. PROCESS HEAT DUTY | | | |
| Total BTU/lb Aromatics | 526 | 446 | 457 |
| Total in MMBTU/hr | 32.0 | 27.1 | 27.8 |
| Energy Saved Over Prior Art, MMBTU/hr | — | 4.9 | 4.2 |
| Energy Saved Over Prior Art, % | — | 15.3 | 13.1 |

In addition to the aspects of the invention disclosed above, those skilled in the art will readily appreciate other variations within the scope of the claims set forth below. For example, the rectification zone can be incorporated into the stripping zone as a single column and provide appropriate internal and external piping to accommodate the flows. Furthermore, the method can incorporate other miscellaneous steps such as washing, mixing, setting, decanting, as well as various purge and make-up streams and heat exchange schemes.

I claim:

1. A continuous solvent extraction-steam-distillation process for the separation of aromatic hydrocarbons from a feedstock comprising non-aromatic hydrocarbons and said aromatic hydrocarbons said process comprising:

(a) contacting said feedstock with a first lean solvent stream and a recycle stream in an extraction zone at super atmospheric pressure to separate said feedstock into a raffinate stream comprising light non-aromatic hydrocarbons and a first rich solvent stream comprising solvent, aromatic hydrocarbons and at least a portion of the light non-aromatic hydrocarbons;

(b) passing the rich solvent stream through a first heat exchanger to proivide a heated rich solvent stream;

(c) passing said heated rich solvent from said first heat exchanger to a stripper zone and operating said stripper zone at a pressure near atmospheric pressure to produce a first vapor stream comprising light non-aromatic hydrocarbons, aromatic hydrocarbons, and water, and to produce a second rich solvent stream;

(d) condensing said first vapor stream and dividing said mixed hydrocarbon phase and a first water rich phase;

(e) passing at least a portion of the mixed hydrocarbon phase extraction zone to provide said recycle stream for step (a);

(f) passing at least a portion of said second rich solvent stream, through second heat exchanger and transferring heat to a wash water stream to generate a stripping steam stream and cooling said second rich solvent stream;

(g) passing said stripping steam stream from said second heat exchanger to a recovery zone and said second rich solvent stream from said second heat exchanger to said recovery zone at a feedpoint and withdrawing a second vapor stream comprising aromatic hydrocarbons and water from the recovery zone;

(h) condensing said second vapor stream and recovering at least a portion of the aromatic hydrocarbon rich phase as an extract product stream;

(i) recovering a second lean solvent stream from the recovery zone of step (g) and passing said second lean solvent stream to an interheater in said recovery zone to transfer at least a portion of the heat from said second lean solvent stream to a liquid within the recovery zone at a point below the feed point, to at least partially reboil the liquid within the recovery zone and to cool the second lean solvent stream, wherein flashing of the heated rich solvent in the stripper zone is reduced resulting in a reduced amount of recycle to the extractor; and (j) passing at least a portion of said second lean solvent stream from said interheater to said first heat exchanger of step (b) to provide said first lean solvent stream and passing said first lean solvent stream from said first heat exchanger to said extraction zone of step (a).

2. The process of claim 1 wherein said solvent comprises polyalkene glycol.

3. The process of claim 2 wherein said solvent comprises tetraethylene glycol.

4. The process of claim 1 wherein said solvent comprises a polyalkylene glycol of the formula:

$$HO-[CHR_1-(CH_2R_3)_n-O-]_mH$$

wherein n is an integer from 1 to 5, m is an integer having a value of 1 or greater and $R_1$, $R_2$ and $R_3$ may each be hydrogen, alkyl, aryl, aralkyl, alkylaryl and mixtures thereof and a glycol ether of the formula:

$$R_4O-[CHR_5-(CHR_6)_xO]_y-R_7$$

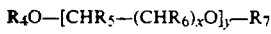

wherein $R_4$, $R_5$, $R_6$ and $R_7$ may each be hydrogen, alkyl, aryl, aralkyl, alkylaryl and mixtures thereof with the proviso that $R_4$ and $R_7$ are not both hydrogen; x is an integer from 1 to 5; and y may be an integer from 2 to 10.

5. The process of claim 4 wherein said solvent consists essentially of a polyalkylene glycol selected from the class consisting of diethylene glycol, triethylene glycol, tetraethylene glycol and mixtures thereof and a glycol ether selected from the class consisting of methoxytriglycol, ethoxytriglycol, butoxytriglycol, methoxytetraglycol and ethoxytetraglycol and mixtures thereof wherein the glycol either comprises between about 0.1 and 99 percentage by weight of the mixed extraction solvent.

6. The process of claim 5 wherein the polyalkylene glycol is tetraethylene glycol and the glycol ether is methoxytriglycol.

7. The process of claim 1 wherein said solvent comprises a sulfolane derivative solvent.

8. The process of claim 1 wherein said solvent comprises sulfolane.

9. The process of claim 1 wherein at least a portion of the liquid within the recovery zone is withdrawn from the column at a withdrawal point located at or below said feedpoint, passed through a third heat exchanger to exchange heat with the second lean solvent stream, and returned as vapor at a point below the withdrawal point.

10. The process according to claim 1 wherein the aromatic hydrocarbon rich phase consists essentially of benzene, toluene and xylene isomers.

11. The process according to claim 1 wherein the aromatic hydrocarbons are separated to produce a toluene fraction and said fraction is blended with other hydrocarbon components to produce finished motor gasoline.

12. The process according to claim 1 wherein an interheater transfers heat form the lean solvent stream to the liquid within the recovery zone.

13. The process of claim 1 wherein said recovery zone operates at a temperature of from 180°–400° F. and the transfer of heat from said lean solvent to said liquid cools said lean solvent to 200°–300° F.

14. The process of claim 1 wherein said stripping zone comprises a separate stripping column and said recovery zone comprises a separate recovery column and said extraction zone comprises a separate extraction column.

15. A continuous solvent extraction-steam-distillation process for the separation of aromatic hydrocarbons from a feedstock comprising non-aromatic hydrocarbons and said aromatic hydrocarbons said process comprising:

(a) contacting said feedstock with a first lean solvent stream and a recycle stream in an extraction column at super atmospheric pressure to separate said feedstock into a raffinate stream comprising light non-aromatic hydrocarbons and a first rich solvent stream comprising solvent, aromatic hydrocarbons and at least a portion of the light non-aromatic hydrocarbons;

(b) passing the rich solvent stream through a first heat exchanger to provide a heated rich solvent stream;

(c) passing said heated rich solvent stream from said first heat exchanger to a stripper zone at a feed point and operating said stripper zone at a pressure near atmospheric pressure to produce a vapor stream comprising light non-aromatic hydrocarbons, aromatic hydrocarbons, and water, and to produce a second rich solvent stream;

(d) condensing said first vapor stream and dividing said vapor into a mixed hydrocarbon phase and a first water rich phase;

(e) passing at least a portion of the mixed hydrocarbon phase to said extraction zone to provide said recycle stream for step (a);

(f) passing at least a portion of said second rich solvent stream, through a second heat exchanger and transferring heat to a wash water stream to generate a stripping steam stream and cooling said second rich solvent stream;

(g) passing said stripping steam stream from said second heat exchanger and said second rich solvent stream to a recovery zone and withdrawing a second vapor stream comprising aromatic hydrocarbons and water from the recovery zone;

(h) condensing said second vapor stream and recovering at least a portion of the aromatic hydrocarbon rich phase as an extract product stream;

(i) recovering a second lean solvent stream from the recovery zone of step (g) and passing said second lean solvent stream to an interheater in said stripper zone to transfer at least a portion of the heat from said second lean solvent stream to a liquid within the stripper zone at a point below the feed point, to at least partially reboil the liquid within the stripper zone and to cool the second lean solvent stream, wherein flashing of the heated rich solvent in the stripper zone is reduced resulting in a reduced amount of recycle to the extractor; and (j) passing at least a portion of said second lean solvent stream from said interheater to said first heat exchanger of step (b) to provide said first lean solvent stream and passing said first lean solvent stream from said first heat exchanger to said extraction zone of step (a).

16. The process of claim 15 wherein said solvent comprises a polyalkene glycol.

17. The process of claim 16 wherein said solvent comprises tetraethylene glycol.

18. The process of claim 15 wherein said solvent comprises a polyalkylene glycol of the formula:

$$HO-[CHR_1-(CH_2R_3)_n-O-]_mH$$

wherein n is an integer from 1 to 5, m is an integer having a value of 1 or greater and $R_1$, $R_2$ and $R_3$ may each be hydrogen, alkyl, aryl, aralkyl, alkylaryl and mixtures thereof and a glycol ether of the formula:

$$R_4O-[CHR_5-(CHR_6)_xO]_y-R_7$$

wherein $R_4$, $R_5$, $R_6$ and $R_7$ may each be hydrogen, alkyl, aryl, aralkyl, alkylaryl and mixtures thereof with the proviso that $R_4$ and $R_7$ are not both hydrogen; x is an integer from 1 to 5; and y may be an integer from 2 to 10.

19. The process of claim 18 wherein said solvent consists essentially of a polyalkylene glycol selected from the class consisting of diethylene glycol, triethylene glycol, tetraethylene glycol and mixtures thereof and a glycol ether selected from the class consisting of methoxytriglycol, ethoxytriglycol, butoxytriglycol, methoxytetraglycol and ethoxytetraglycol and mixtures thereof wherein the glycol either comprises between about 0.1 and 99 percentage by weight of the mixed extraction solvent.

20. The process of claim 19 wherein the polyalkylene glycol is tetraethylene glycol and the glycol ether is methoxytriglycol.

21. The process of claim 15 wherein said solvent comprises a sulfolane derivative solvent.

22. The method of claim 15 wherein said solvent comprises sulfolane.

23. The process of claim 15 wherein at least a portion of the liquid within the stripper column is withdrawn from the column at a draw point located at or below said feedpoint, passed through a third heat exchanger to exchange heat with the second lean solvent stream, and returned as vapor at a point below the withdrawal point.

24. The process according to claim 15 wherein an interheater transfers heat from the lean solvent to the liquid within the recovery zone.

25. The process of claim 15 wherein said recovery zone operates at a temperature of from 180°–400° F. and the transfer of heat from said lean solvent to said liquid cools said lean solvent to 200°–300° F.

26. The process of claim 15 wherein said stripping zone comprises a separate stripping column and said recovery zone comprises a separate recovery column and said extraction zone comprises a separate extraction column.

27. The process according to claim 15 wherein the aromatic hydrocarbons consist essentially of benzene, toluene, and xylene isomers and said aromatics are separated to produce a toluene fraction and said toluene fraction is blended with other hydrocarbon components to produce finished motor gasoline.

28. A continuous solvent extraction-steam-distillation process for the separation of aromatic hydrocarbons in the range of $C_6$–$C_{12}$ from a feedstock comprising non-aromatic hydrocarbons in the range of $C_5$–$C_{12}$ and said aromatic hydrocarbons said process comprising:

(a) contacting said feedstock with a first lean solvent stream and a recycle stream in an extractor column at super atmospheric pressure to separate said feedstock into an overhead raffinate stream comprising light non-aromatic hydrocarbons and a bottoms stream providing a first rich solvent stream comprising substantially all of the solvent, substantially all of the aromatic hydrocarbons and at least a portion of the light non-aromatic hydrocarbons;

(b) passing the rich solvent stream through a first heat exchanger to provide a heated rich solvent stream;

(c) passing said heated rich solvent stream from said first heat exchanger to a stripper column and operating said stripper column at a pressure near atmospheric pressure to produce a first overhead vapor stream comprising light non-aromatic hydrocarbons, aromatic hydro-carbons, and water, and to produce a second rich solvent stream from the bottom of the column;

(d) condensing said first vapor stream and dividing said vapor into a mixed hydrocarbon phase and a first water rich phase;

(e) passing at least a portion of the mixed hydrocarbon phase to said extractor column to provide said recycle stream at a point in said extractor column between the entry point of the feedstock and the bottom of said column according to step (a);

(f) passing at least a portion of said second rich solvent stream, through a second heat exchanger and transferring heat to a spent wash water stream to generate a stripping steam stream and to cool said second rich solvent stream;

(g) passing said stripping steam stream from said second heat exchanger to the bottom of a recovery column and passing said second rich solvent stream from said second heat exchanger to said recovery column at a feedpoint and withdrawing a second vapor stream comprising aromatic hydrocarbons and water from the recovery column;

(h) condensing said second vapor stream and dividing said second vapor stream into an aromatic hydrocarbon rich phase and a second water rich phase and recovering at least a portion of the aromatic hydrocarbon rich phase as an extract product stream;

(i) passing said raffinate stream from step (a) to a feedpoint near the bottom of a raffinate column and contacting said raffinate with the second water rich phase introduced near the top of said raffinate column to wash said raffinate stream;

(j) recovering a second lean solvent stream from the bottom of the recovery column of step (g) and passing said second lean solvent stream to an interheater in said recovery column to transfer at least a portion of the heat from said second lean solvent stream to a liquid within the recovery column at a point below the feed point, to at least partially reboil the liquid within the recovery column and to cool the second lean solvent stream, wherein flashing of the heated rich solvent in the stripper column is reduced resulting in a reduced amount of recycle to the extractor; and (l) passing at least a portion of said second lean solvent stream from said interheater to said first heat exchanger of step (b) to provide said first lean solvent stream and passing said first lean solvent stream from said first heat exchanger to a feedpoint near the top of said extractor column of step (a).

29. The process of claim 28 wherein said solvent comprises sulfolane.

30. The process of claim 29 wherein said solvent comprises tetraethylene glycol.

31. A continuous solvent extraction-steam-distillation process for the separation of aromatic hydrocarbons from a feedstock comprising non-aromatic hydrocarbons and said aromatic hydrocarbons comprising:

(a) contacting said feedstock with a first lean solvent stream and a recycle stream in an extractor column at super atmospheric pressure to separate said feedstock into an overhead raffinate stream comprising light non-aromatic hydrocarbons and a bottoms first rich solvent stream comprising substantially all of the solvent, substantially all of the aromatic hydrocarbons, and at least a portion of the light non-aromatic hydrocarbons;

(b) passing the rich solvent stream through a first heat exchanger to provide a heated rich solvent stream;

(c) passing said heated rich solvent stream from said first heat exchanger to a stripper column at a feedpoint and operating said stripper column at a pressure near atmospheric pressure to produce a vapor stream comprising light non-aromatic hydrocarbons, aromatic hydrocarbons, and water, and to produce a second rich solvent stream from the bottom of the column;

(d) condensing said first vapor stream and dividing said vapor into a mixed hydrocarbon phase and a first water rich phase;

(e) passing at least a portion of the mixed hydrocarbon phase to said extractor column to provide said recycle stream at a point in said extractor column between the entry point of the feedstock and the bottom of said extractor column according to step (a);

(f) passing at least a portion of said second rich solvent stream, through a second heat exchanger and transferring heat to a spent wash water stream to generate a stripping steam and cooling said second rich solvent stream;

(g) passing said stripping steam stream from said second heat exchanger to the bottom of a recovery column and passing said second rich solvent stream to said recovery column and withdrawing a second vapor stream comprising aromatic hydrocarbons and water from the recovery column;

(h) condensing said second vapor stream and dividing said second vapor stream into an aromatic hydrocarbon rich phase and a second water rich phase and recovering at least a portion of the aromatic hydrocarbon rich phase as an extract product stream;

(i) passing said raffinate stream from step (a) to a feedpoint near the bottom of a raffinate column and contacting said raffinate with the second water rich phase introduced near the top of said raffinate column to wash said raffinate stream;

(j) recovering a second lean solvent stream from the bottom of the recovery column of step (g) and passing said second lean solvent stream to an interheater in said recovery column to transfer at least a portion of the heat from said second lean solvent stream to a liquid within the stripper column at a point below the feed point, to at least partially reboil the liquid within the recovery column and to cool the second lean solvent stream, wherein flashing of the heated rich solvent in the stripper column is reduced resulting in a reduced amount of recycle to the extractor; and (l) passing at least a portion of said second lean solvent stream from said interheater to said first heat exchanger of step (b) to provide said first lean solvent stream and passing said first lean solvent stream from said first heat exchanger to a feedpoint near the top of said extractor column of step (a).

32. The process of claim 31 wherein said solvent comprises sulfolane.

33. The process of claim 31 wherein said solvent comprises tetraethylene glycol.

34. The process of claim 1 wherein the reduced amount of recycle to the extractor in step (i) is less than about 0.34 weight units of recycle per weight units of feedstock.

* * * * *

UNITED STATES PATENT AND TRADEMARK OFFICE
CERTIFICATE OF CORRECTION

PATENT NO. : 5,176,821
DATED : January 5, 1993
INVENTOR(S) : Paulino Forte

It is certified that error appears in the above-identified patent and that said Letters Patent is hereby corrected as shown below:

In Column 14, line 67: Insert "vapor into a" before -- mixed --;

In Column 15, line 2: Insert "to said" before -- extraction --;

In Column 15, line 5: Insert "a" before -- second --.

Signed and Sealed this

Sixteenth Day of November, 1993

Attest:

BRUCE LEHMAN

Attesting Officer

Commissioner of Patents and Trademarks